US00PP11534P

United States Patent [19]

Kientzler

[11] Patent Number: Plant 11,534

[45] Date of Patent: Oct. 3, 2000

[54] NEW GUINEA IMPATIENS PLANT NAMED 'KIJUAN'

[75] Inventor: Ludwig Kientzler, Gensingen, Germany

[73] Assignee: Paul Ecke Ranch, Encinitas, Calif.

[21] Appl. No.: 09/093,168

[22] Filed: Jun. 8, 1998

[51] Int. Cl.[7] ..... A01H 5/00

[52] U.S. Cl. ..... Plt./318

[58] Field of Search ..... Plt./318

[56] References Cited

U.S. PATENT DOCUMENTS

| | | | |
|---|---|---|---|
| P.P. 7,670 | 10/1991 | Guillen | Plt./318 |
| P.P. 7,791 | 2/1992 | Drewlow | Plt./318 |
| P.P. 10,495 | 7/1998 | Danziger | Plt./318 |

*Primary Examiner*—Howard J. Locker
*Assistant Examiner*—Kent L. Bell
*Attorney, Agent, or Firm*—C. A. Whealy

[57] ABSTRACT

A new and distinct cultivar of New Guinea Impatiens plant named 'Kijuan', characterized by its small and numerous blush pink-colored flowers; compact, upright and outwardly spreading growth habit; freely branching plant habit; and narrow dark green slightly glossy non-variegated leaves.

1 Drawing Sheet

BACKGROUND OF THE INVENTION

The present invention relates to a new and distinct cultivar of New Guinea Impatiens plant, botanically known as *Impatiens hawkeri*, previously known under the code name, MF 338 Blush, and hereinafter referred to by the cultivar name 'Kijuan'.

The new cultivar is a product of a planned breeding program conducted by the Inventor in Gensingen, Germany. The objective of the breeding program was to develop compact varieties with numerous small flowers, early-flowering, uniform plant habit, attractive flower and foliage colors and good flower form.

The new cultivar originated from a cross made by the Inventor of the proprietary selection identified as MF 571 as the male, or pollen parent, with the proprietary selection identified as MF 22 as the female, or seed parent. The cultivar 'Kijuan' was discovered and selected by the Inventor as a flowering plant within the progeny of the stated cross in a controlled environment in Gensingen, Germany, in April, 1996. Asexual reproduction of the new cultivar by terminal cuttings taken at Gensingen, Germany, has shown that the unique features of this new Impatiens are stable and reproduced true to type in successive generations of asexual reproduction.

SUMMARY OF THE INVENTION

The following traits have been repeatedly observed and are determined to be the unique characteristics of 'Kijuan'. These characteristics in combination distinguish 'Kijuan' as a new and distinct cultivar:

1. Small and numerous blush pink-colored flowers.

2. Compact, upright and outwardly spreading growth habit.

3. Freely branching plant habit.

4. Narrow dark green, slightly glossy non-variegated leaves.

Plants of the new New Guinea Impatiens have darker green foliage and lighter flower color than plants of the male parent, MF 571. Compared to plants of the female parent, MF 22, plants of the new New Guinea Impatiens are larger and have darker pink and more rounded flowers.

Plants of the new New Guinea Impatiens are similar in flower color to the New Guinea Impatiens cultivar 'Apple Blossom' (disclosed in U.S. Plant Pat. No. 10,111). However in side-by-side comparisons in Encinitas, Calif., under commercial practice, plants of the new New Guinea Impatiens differed from plants of the cultivar 'Apple Blossom' in the following characteristics:

1. Plants of the new New Guinea Impatiens are more compact than plants of the cultivar 'Apple Blossom'.

2. Leaves of plants of the new New Guinea Impatiens are darker green and more narrow than leaves of plants of the cultivar 'Apple Blossom'.

3. Leaf petioles of plants of the new New Guinea Impatiens are shorter than leaf petioles of plants of the cultivar 'Apple Blossom'.

4. Flowers of plants of the new New Guinea Impatiens are held above the foliage whereas flowers of plants of the cultivar 'Apple Blossom' are held at canopy level or slightly below.

5. Flowers of plants of the new New Guinea Impatiens are smaller and have a less distinct "eye" at the center of the flower than flowers of plants of the cultivar 'Apple Blossom'.

6. Flower peduncles of plants of the new New Guinea Impatiens are longer than flower peduncles of plants of the cultivar 'Apple Blossom'.

A detailed comparison of plants of the new New Guinea Impatiens and the cultivar 'Apple Blossom' appears in Chart A at the end of the specification.

BRIEF DESCRIPTION OF THE PHOTOGRAPHS

The accompanying colored photographs illustrate the overall appearance of the new cultivar, showing the colors as true as it is reasonably possible to obtain in colored reproductions of this type.

The photograph at the top of the sheet comprises a side perspective view of a typical plant of 'Kijuan'.

The photograph at the bottom of the sheet comprises a close-up view of a typical flower and leaves of 'Kijuan'. Flower and foliage colors in the photographs may differ from the actual colors due to light reflectance.

DETAILED BOTANICAL DESCRIPTION

The cultivar 'Kijuan' has not been observed under all possible environmental conditions. The phenotype may vary somewhat with variations in environment such as temperature and light intensity, without, however, any variance in genotype. The following observations, measurements and comparisons describe plants grown in 10-cm pots in Encinitas, Calif., under commercial practice in a fiberglass-covered greenhouse with day temperatures ranging from 23 to 29° C. and night temperatures ranging from 16 to 18° C. and light levels of about 3,000 footcandles.

In the following description, color references are made to The Royal Horticultural Society Colour Chart except where general terms of ordinary dictionary significance are used.

Classification:

*Botanical.*—*Impatiens hawkeri* cultivar 'Kijuan'.

*Commercial.*—New Guinea Impatiens cultivar 'Kijuan'.

Parentage:

*Male parent.*—Proprietary selection of *Impatiens hawkeri* identified as MF 571.

*Female parent.*—Proprietary selection of *Impatiens hawkeri* identified as MF 22.

Propagation:

*Type cutting.*—Terminal cuttings.

*Time to initiate roots.*—Summer: About 14 days with 21° C. soil temperature. Winter: About 18 days with 21° C. soil temperature.

*Time to develop roots.*—Summer: About 21 days with 21° C. soil temperature. Winter: About 24 days with 21° C. soil temperature.

Plant description:

*Plant form.*—Upright and outwardly spreading, rounded and mounding.

*Growth habit.*—Moderately vigorous. Moderate branching, dense and bushy growth. Appropriate for 10 and 12.5-cm containers.

*Crop time.*—From planting of a rooted cutting, about six to eight weeks are required to produce a finished flowering plant in a 12.5-cm container.

*Plant size.*—Height: About 11 cm. Width or spread: About 20 cm.

*Lateral branches.*—Quantity: About five. Length: About 10 cm. Diameter: About 1.1 cm. Internode length: About 3 cm. Color: 59B.

*Foliage description.*—Leaves simple, generally symmetrical, abundant, opposite or in whorls of three, horizontal to plant and flat in aspect. Length: About 10 cm. Width: About 3.1 cm. Shape: Elliptic with acuminate apex, attenuate base and serulate margin with ciliation. Texture: Smooth, slightly glossy. Color: Young foliage, upper surface: 146A. Young foliage, lower surface: 147B. Fully expanded foliage, upper surface: 147A. Fully expanded foliage, lower surface: 147C. Venation, upper surface: Close to 147C with reddish tinge, 59D. Venation, lower surface: 60B. Petiole: Length: About 2.5 cm. Diameter: About 3 mm. Color: 60C.

Flower description:

*Flower type and habit.*—Small blush pink-colored flowers. Freely and continuously flowering. Flowers arise from leaf axils. Usually about seven flowers per lateral branch and typically about 26 flowers and flower buds per plant. Flowers positioned above the foliage and face outward. Flowers flat and slightly oblong. Flowers persistent.

*Flowering season.*—Year-round under greenhouse conditions. In the garden, flowering is continuous from spring until fall. Flowers typically last less than one week depending on environmental and cultural conditions.

*Flower size.*—Length: About 4.5 cm. Width: About 4 cm. Depth: About 4 mm.

*Flower buds.*—Length: About 1.8 cm. Diameter: About 1.3 cm. Shape: Ovoid. Color: 65A with dark purple, 59B, dorsal ridge.

*Petals.*—Quantity: Five. Length: Upper petal: About 2.5 cm. Middle petals: About 2.2 cm. Lower petals: About 2.7 cm. Width: Upper petal: About 3.5 cm. Middle petals: About 2.4 cm. Lower petals: About 2.7 cm. Shape: Cordate with emarginate apex, acute base and entire margin. Texture: Velvety, smooth. Color: When opening, upper surface: 65B. When opening, lower surface: 62A. Fully opened, upper surface: Margins and upper petal midvein: 65A. Center: 65C. Base or eye: 66B. Fully opened, lower surface: 65B/65C. Fading to: 65C.

*Spur.*—Length: About 3.9 cm. Shape: Narrow and curved. Color: 59A.

*Peduncles.*—Length: About 5 cm. Angle: Erect and outward. Strength: Moderately strong. Color: 59B.

*Reproductive organs.*—Androecium: Stamen number: Five, anthers fused, filaments free. Anther shape: Obovate. Anther size: 4 mm by 5 mm. Anther color: 63A. Amount of pollen: Moderate. Pollen color: Creamy white. Gynoecium: Five-loculate fused. Gynoecium length: About 4 mm. Gynoecium color: 146D.

Disease resistance:

Under commercial conditions, resistance to pathogens has not been observed.

Seed development:

Seed production has not been observed.

CHART A

| CHARACTERISTIC | 'KIJUAN' | 'APPLE BLOSSOM' |
|---|---|---|
| PLANT HEIGHT | About 11 cm | About 12.5 cm |
| LEAF WIDTH | About 3.1 cm | About 3.7 cm |
| LEAF COLOR, FULLY EXPANDED, UPPER SURFACE | 147A | 146A |
| VENATION COLOR, UPPER SURFACE | 59D | 63B |
| VENATION COLOR, LOWER SURFACE | 60B | 63A |
| PETIOLE LENGTH | About 2.5 cm | About 3.25 cm |
| FLOWERING HABIT | Above foliage | At canopy or below |
| FLOWER SHAPE | Oblong | Rounded triangular |
| FLOWER SIZE (length by width) | About 4.5 cm by 4 cm | About 4.9 cm by 4.9 cm |
| SPUR LENGTH | About 3.9 cm | About 4.3 cm |
| PETAL APPEARANCE | Velvety | Iridescent |
| PETAL COLOR, WHEN | 65B | 62A |

CHART A-continued

| CHARACTERISTIC | 'KIJUAN' | 'APPLE BLOSSOM' |
|---|---|---|
| OPENING, UPPER SURFACE | | |
| PETAL COLOR, WHEN OPENING LOWER SURFACE | 62A | 58D |
| PETAL COLOR, OPENED, UPPER SURFACE | Margins, 65A<br>Center, 65C<br>Eye, 66B | Center, 62A/62B/62C<br>Eye, 66B |
| PETAL COLOR, OPENED, LOWER SURFACE | 65B/65C | 62A |
| PETAL COLOR, FADING TO | 65C | 62B/62C |
| PEDUNCLE LENGTH | About 5 cm | About 4.3 cm |

It is claimed:

1. A new and distinct cultivar of New Guinea Impatiens plant named 'Kijuan', as illustrated and described.

* * * * *

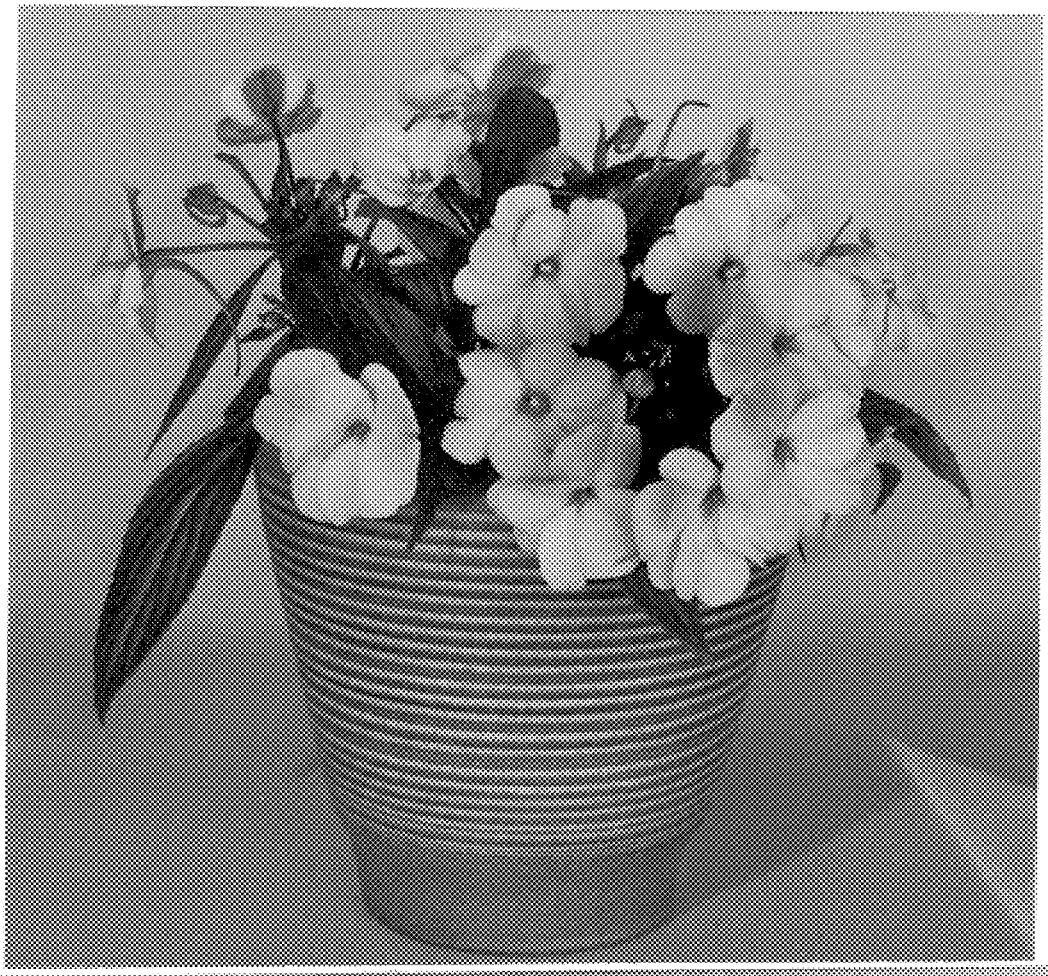
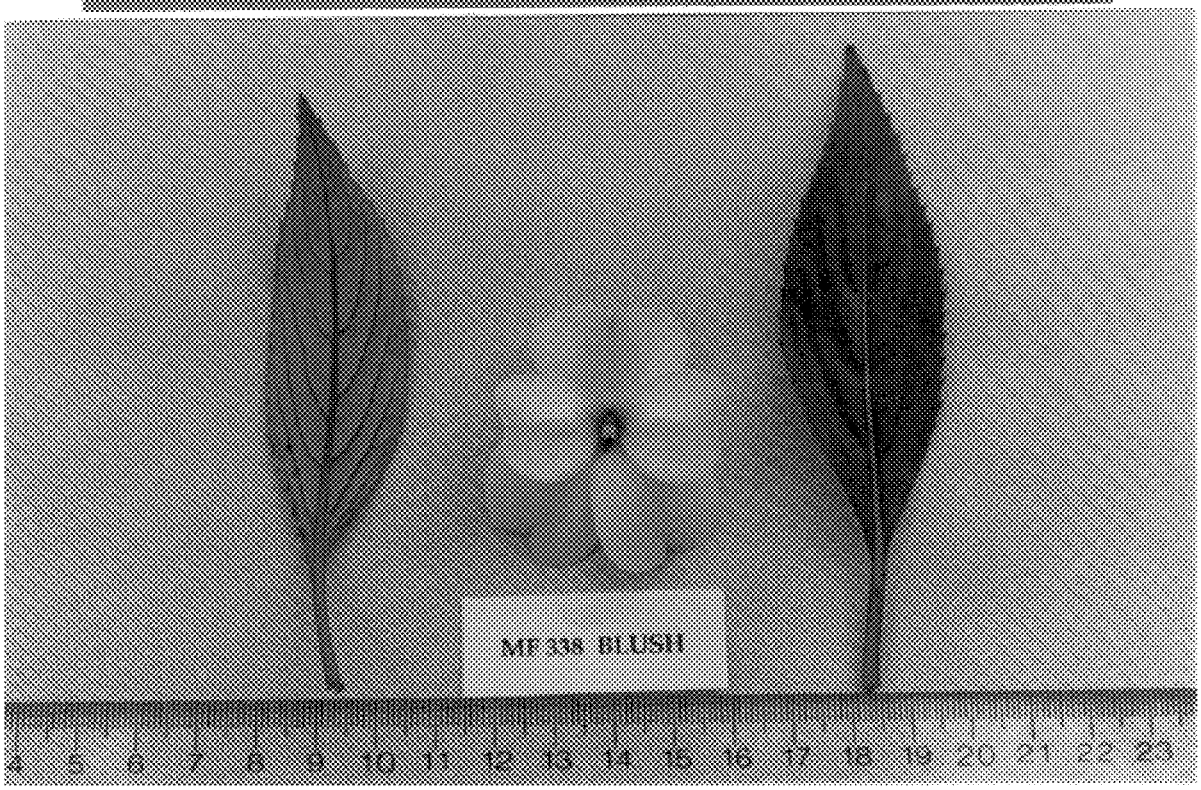
MF 338 BLUSH
4 5 6 7 8 9 10 11 12 13 14 15 16 17 18 19 20 21 22 23